United States Patent [19]

Dickson

[11] Plant 4,991

[45] Mar. 15, 1983

[54] ROSE PLANT

[75] Inventor: A. Patrick C. Dickson, Newtownards, Northern Ireland

[73] Assignee: Jackson & Perkins Company, Medford, Oreg.

[21] Appl. No.: 301,382

[22] Filed: Sep. 11, 1981

[51] Int. Cl.[3] ..... A01H 5/00

[52] U.S. Cl. ..... Plt./9

[58] Field of Search ..... Plt./7, 9

*Primary Examiner*—Robert E. Bagwill

*Attorney, Agent, or Firm*—Klarquist, Sparkman, Campbell, Leigh, Whinston & Dellett

[57] ABSTRACT

A miniature rose variety having a well branched, upright plant; orange-colored buds turning to light pink flowers; little or no fragrance.

1 Drawing Figure

This present invention relates to a new and distinct variety of rose plant of the miniature class which was originated by me by crossing an unnamed variety, which itself was a cross between the variety Bangor and the variety Anabell (otherwise known as Korbell), with the pollen of the variety Nozomi.

The primary objective of this breeding was to produce a new miniature rose variety of upright habit, compact growth, and clean foliage with buds and blooms of an orange color. This objective was substantially achieved along with other desirable improvements as evidenced by the following unique combination of characteristics which are outstanding in the new variety and which distinguish it from its parents as well as from all other varieties of which I am aware:

1. Well branched, upright plant reaching less than 24" after one year's growth.
2. Orange colored buds turning to light pink in the aged open flowers.
3. Strong resistance to rose powdery mildew.
4. Few thorns.
5. Little or no fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed (Bangor × Anabell).

*Pollen parent.*—Nozomi.

Classification:

*Botanical.*—Rosa hybrid.

*Commercial.*—Miniature.

FLOWER

Observations made from specimens grown in a greenhouse at Irvine, Calif. in January.

Blooming habit: Continuous.

Bud:

*Size.*—Approximately ½" when petals start to unfurl.

*Form.*—Pointed ovoid.

*Color.*—When sepals first divide, Near Orange-Red 31B; when half blown, upper side of petals Near Orange 29B, except outer petals near Pink, Red Group 38C, lower side of petals Near Orange 29B.

*Sepals.*—Color: Outer surface Green 138C; three appendaged sepals heavily appendaged, lightly glandular; two unappendaged sepals hairy edged, lightly glandular.

*Receptacle.*—Color: Green 138C. Shape: Funnel. Size: Large. Surface: Hairy, short pubescence.

*Peduncle.*—Length: Medium. Surface: Glandular. Color: Light green. Strength: Stiff, erect, slender.

*Opening.*—Petals fold outward and remain flat with slightly recurved edges.

Bloom:

*Size.*—Medium. Average open size 1½".

*Borne.*—In clusters, irregular.

*Stems.*—Short.

*Form.*—When first open, cupped. Permanence: Outer petal edges slightly curled.

*Petalage.*—Number of petals under normal conditions: 30–35.

*Color.*—Center of flower: Upper side of petals Orange 29B. Reverse side of petals Orange 29B. Base of petals Yellow 12B. General tonality from a distance Orange 29B.

*Variegations.*—None.

*Discloration.*—General tonality at end of first day: Outer petals begin to change to pink; third day or later, color becomes a pink near Red Group 38C and D.

*Fragrance.*—None.

Petals:

*Texture.*—Thin.

*Shape.*—Obovate.

*Form.*—Tips slightly recurved, edges slightly quilled.

*Arrangement.*—Irregular, informal. Petaloids in center, few.

*Persistence.*—Drop off cleanly.

*Lastingness.*—On the plant, long. As cut flower, long.

Reproductive parts:

*Anthers.*—Medium. Color: Yellow. Arrangement: Regular around styles.

*Filaments.*—Color: Yellow.

*Pollen.*—Lemon yellow.

*Styles.*—Color: Pink.

*Stigmas.*—Color: White.

Form: Bush.

Growth: Vigorous, upright, compact. Miniature type, reaching less than 24" in height in first year of growth.

Foliage:

*Number of leaflets on normal mid-stem leaves.*—Usually 5, with numerous entire bracts below the flowers.

*Size.*—Small.

*Quantity.*—Normal.

*Color.*—New foliage: Light green, near 139C overlaid with Greyed Purple 187C. Old foliage: Green 139A.

Leaflets:

*Shape.*—Oval pointed.

*Texture.*—Leathery.

*Edge.*—Serrated.

*Serration.*—Single, large.

*Petiole.*—Rachis: Color, reddish. Underside: Prickles.

*Stipules.*—Long.

*Disease resistance.*—Resistant to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, few. On laterals from stalk, few.

*Form.*—Narrow base, long, hooked downward.

*Color when young.*—Brown.

*Position.*—Irregular.

Small prickles:

*Quantity.*—On main stalks, none. On laterals, none.

I claim:

1. A new and distinct variety of rose plant of the miniature class, substantially as herein shown and described, characterized particularly as to novelty by the unique combination of its heavily branched, upright miniature plant bearing orange colored buds opening to pink mature flowers with no fragrance, and its resistance to rose powdery mildew.

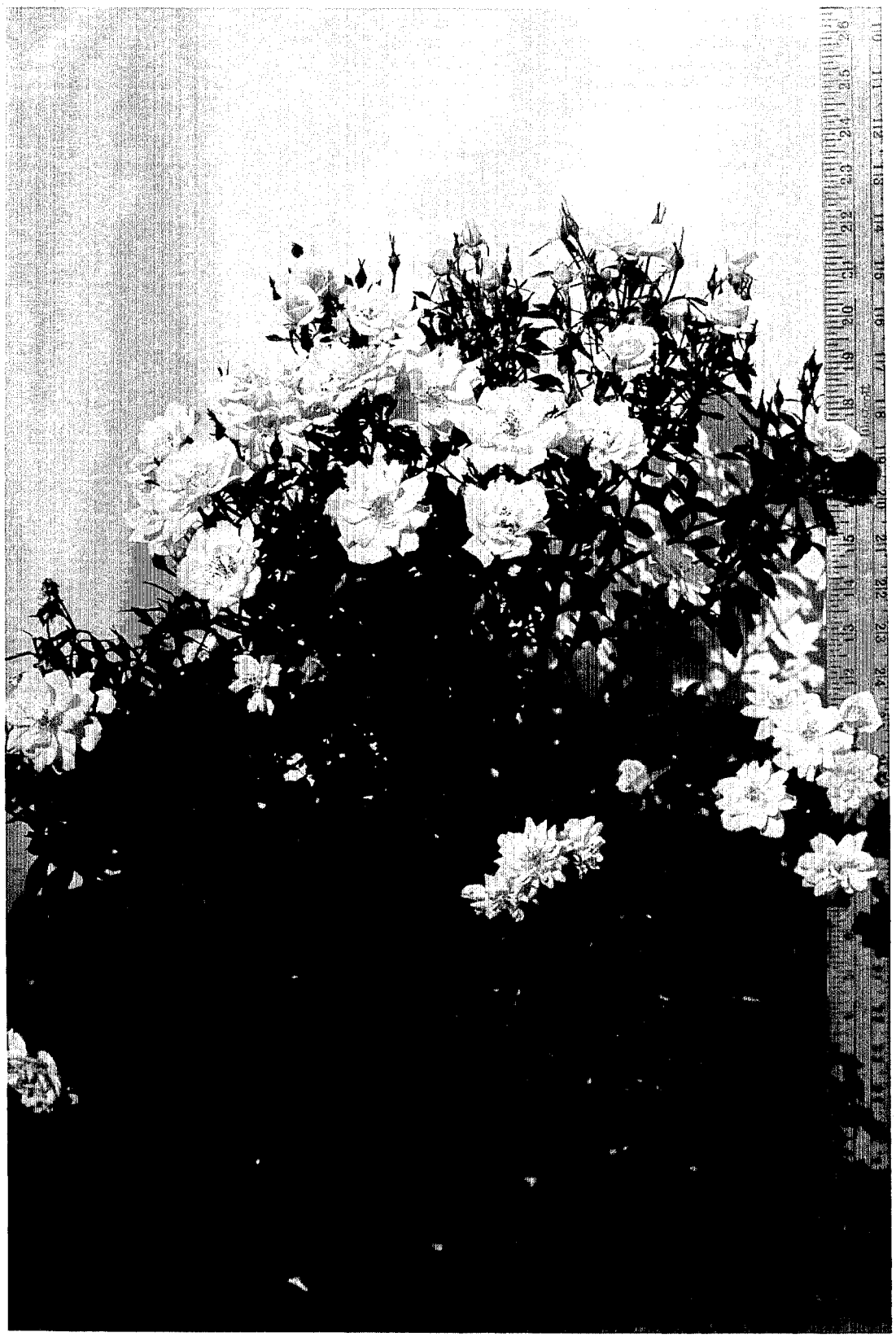

* * * * *